(12) United States Patent
Goupil et al.

(10) Patent No.: US 6,652,883 B2
(45) Date of Patent: Nov. 25, 2003

(54) TISSUE BULKING AND COATING COMPOSITIONS

(75) Inventors: Dennis W. Goupil, Norcross, GA (US); Hassan Chaouk, Atlanta, GA (US); Troy Holland, Suwanee, GA (US); Bruktawit T. Asfaw, Atlanta, GA (US); Stephen D. Goodrich, Norcross, GA (US); Lucas Latini, Norcross, GA (US)

(73) Assignee: BioCure, Inc., Norcross, GA (US)

( * ) Notice: Subject to any disclaimer, the term of this patent is extended or adjusted under 35 U.S.C. 154(b) by 0 days.

(21) Appl. No.: 09/804,925

(22) Filed: Mar. 13, 2001

(65) Prior Publication Data

US 2001/0051670 A1 Dec. 13, 2001

Related U.S. Application Data

(60) Provisional application No. 60/188,975, filed on Mar. 13, 2000.

(51) Int. Cl.$^7$ .................................................. A61K 9/14
(52) U.S. Cl. ...................... 424/489; 424/499; 424/501; 424/9.1; 424/422; 424/423; 424/424; 424/425; 424/426; 424/484; 424/486; 514/772; 514/772.1; 514/772.2
(58) Field of Search ................................. 424/422, 423, 424/489, 501, 499, 9.1, 424, 425, 426, 484, 486; 514/772, 772.1, 772.2

(56) References Cited

U.S. PATENT DOCUMENTS

| | | |
|---|---|---|
| 5,047,055 A | 9/1991 | Bao et al. |
| 5,278,202 A | 1/1994 | Dunn et al. |
| 5,344,452 A | 9/1994 | Lemperle |
| 5,410,016 A | 4/1995 | Hubbell et al. |
| 5,490,984 A | 2/1996 | Freed |
| 5,508,317 A | 4/1996 | Muller |
| 5,514,379 A | 5/1996 | Weissleder et al. |
| 5,529,914 A | 6/1996 | Hubbell et al. |
| 5,709,854 A | 1/1998 | Griffith-Cima et al. |
| 5,844,016 A | 12/1998 | Sawhney et al. |
| 5,879,713 A | 3/1999 | Roth et al. |
| 5,902,599 A | 5/1999 | Anseth et al. |
| 5,932,674 A | 8/1999 | Muller |
| 5,942,209 A | 8/1999 | Leavitt et al. |
| 5,981,826 A | 11/1999 | Ku et al. |
| 6,028,164 A | 2/2000 | Loomis |
| 6,037,366 A | 3/2000 | Krall et al. |
| 6,060,534 A | 5/2000 | Ronan et al. |
| 6,083,524 A | 7/2000 | Sawhney et al. |
| 6,129,761 A | 10/2000 | Hubbell |
| 6,153,211 A | 11/2000 | Hubbell et al. |
| 6,166,130 A | 12/2000 | Rhee et al. |
| 6,191,193 B1 | 2/2001 | Lee et al. |
| 6,201,065 B1 | 3/2001 | Pathak et al. |
| 6,265,509 B1 * | 7/2001 | Muller ....................... 526/266 |

FOREIGN PATENT DOCUMENTS

| | | |
|---|---|---|
| EP | 730 847 | 5/2001 |
| WO | WO 95/09659 | 4/1995 |
| WO | WO 97/22371 | 6/1997 |
| WO | WO 97/22372 | 6/1997 |
| WO | WO 98/17200 | 4/1998 |
| WO | WO 98/17201 | 4/1998 |
| WO | WO 99/12577 | 3/1999 |
| WO | WO 99/44643 | 9/1999 |
| WO | WO 00/09087 | 2/2000 |
| WO | WO 00/09088 | 2/2000 |
| WO | WO 00/09190 | 2/2000 |
| WO | WO 00/09199 | 2/2000 |
| WO | WO 00/23054 | 4/2000 |
| WO | WO 00/35373 | 6/2000 |
| WO | WO 00/50103 | 8/2000 |
| WO | WO 00/62827 | 1/2001 |
| WO | WO 01/16210 | 3/2001 |
| WO | WO 01/17574 | 3/2001 |
| WO | WO 00/64977 | 5/2001 |
| WO | WO 01/44307 | 6/2001 |
| WO | WO 01/55360 | 8/2001 |
| WO | WO 01/70132 | 9/2001 |
| WO | WO 01/70289 | 9/2001 |
| WO | WO 01/70290 | 9/2001 |
| WO | WO 01/70291 | 9/2001 |
| WO | WO 02/16443 | 2/2002 |

OTHER PUBLICATIONS

Thanoo BC et al., J. Pharm. Pharmacol. 45:16–20 (1993).

* cited by examiner

*Primary Examiner*—Thurman K. Page
*Assistant Examiner*—Liliana Di Nola-Baron
(74) *Attorney, Agent, or Firm*—Collen A. Beard

(57) ABSTRACT

Compositions comprising macromers having a backbone comprising units having a 1,2-diol and/or 1,3-diol structure for tissue bulking and coating. Such polymers include poly (vinyl alcohol) (PVA) and hydrolyzed copolymers of vinyl acetate, for example, copolymers with vinyl chloride, N-vinylpyrrolidone, etc. The backbone polymer contains pendant chains bearing crosslinkable groups and, optionally, other modifiers. When crosslinked, the macromers form hydrogels having many properties advantageous for use as agents to bulk and coat tissues.

13 Claims, No Drawings

TISSUE BULKING AND COATING COMPOSITIONS

RELATED APPLICATION

This application claims priority to U.S. Ser. No. 60/188,975, filed on Mar. 13, 2000.

BACKGROUND OF THE INVENTION

The invention relates to compositions for use in tissue bulking and coating. More specifically, the invention relates to compositions including crosslinkable macromonomers (also referred to herein as macromers) that form hydrogels useful in tissue bulking and coating. The invention also relates to methods for tissue bulking and coating.

There are many instances in which an appropriate biomaterial is needed for use in repair of tissues and in augmentation of tissues. Applications for an appropriate biomaterial include repair of defects and conditions in a tissue caused by disease, injury, or aging, repair of congenital defects and conditions in a tissue, and augmentation of tissues to provide a desirable functional, reconstructive, or cosmetic change. Biomaterials are also needed for sealing tissues to prevent post operation leakage, for tissue adherence, and for prevention of tissue adhesion. Biomaterials are also needed for cell encapsulation for forming bioreactors, for example, and for cell implantation.

Gastroesophageal reflux is a physical condition in which stomach acids reflux, or flow back from the stomach into the esophagus. Frequent reflux episodes (two or more times per week), may result in a more severe problem known as gastroesophageal reflux disease (GERD). The primary cause of GERD is believed to be the lack of competency of the lower esophageal sphincter. The lower esophageal sphincter, or valve, is comprised of smooth muscle located at the gastroesophageal (GE) junction and functions to allow food and liquid to pass into the stomach but prevent regurgitation of stomach contents. Bulking of the lower esophageal sphincter may be beneficial.

Vesicoureteral reflux is a condition wherein there is an abnormal development of the ureteral bud as it enters the bladder during embryologic development. The shortened course of the ureter through the bladder musculature decreases the ureteral resistance and allows for urine to reflux from the bladder reservoir back up into the ureter and into the kidney. Vesicoureteral reflux can be treated by endoscopic injection of a bulking agent in the submucosal space. Generally, a cystoscope is inserted into the bladder, a needle is inserted through the cystoscope and placed under direct vision underneath the refluxing ureter in the submucosal space, and the bulking agent is injected until the gaping ureteric orifice configuration changes into a half-moon slit.

Urinary incontinence is the inability to retain urine and not void urine involuntarily. As a person ages, his ability to voluntarily control the sphincter muscle is lost in the same way that general muscle tone deteriorates with age. This can also occur when a radical event such as paraplegia "disconnects" the parasympathetic nervous system causing a loss of sphincter control. Some types of incontinence can be treated by injection of a bulking agent into the submucosa of the urethra, in order to "beef up" the area and improve muscle tone.

Biomaterials are used in a number of applications in the field of plastic and reconstructive surgery. For example, various compositions have been used for implantation in the lips and to fill in wrinkles. Biomaterials have also been used as breast implants, typically encased within a silicone shell.

Biomaterials have been used in repair of hard tissue such as cartilage and bone. Musculoskeletal damage can occur due to injury or decay and can be repaired, in some cases, by replacement of the damaged tissue with an appropriate biomaterial.

In many tissue repair and augmentation applications, the ideal biomaterial should be easy to inject, well tolerated, not reabsorbed, and not prone to migration. In some cases, it may be desirable for the biomaterial to degrade and be absorbed over a period of time. In some applications, it may be desirable to form the implant ex vivo. In such cases, the biomaterial need not be injectable.

SUMMARY OF THE INVENTION

The invention relates to compositions for use in tissue bulking and coating. More specifically, the invention relates to compositions including crosslinkable macromonomers (also referred to herein as macromers) that form hydrogels useful in tissue bulking and coating. The invention also relates to methods for tissue bulking and coating.

The compositions include macromers having a backbone of a polymer having units with a 1,2-diol and/or 1,3-diol structure. Such polymers include poly(vinyl alcohol) (PVA) and hydrolyzed copolymers of vinyl acetate, for example, copolymers with vinyl chloride, N-vinylpyrrolidone, etc. The backbone polymer contains pendant chains bearing crosslinkable groups and, optionally, other modifiers. When crosslinked, the macromers form hydrogels having many properties advantageous for use as agents to bulk and coat tissues.

The compositions can be used for a variety of applications such as, but not limited to, bulking of the lower esophageal sphincter to treat GERD, urethral bulking to treat urinary incontinence, bulking of the ureteral to treat vesicoureteral reflux, esophageal bulking, tissue reconstruction due to injury or disease (i.e. reconstruction of a breast after partial mastectomy), tissue augmentation, and spinal disc replacement.

In one embodiment, the composition forms a permanent mass. In another embodiment, the composition forms a temporary or reversible (the terms temporary and reversible are herein used interchangeably) mass. Temporary bulking may be desired, for example, when using the composition in combination with cells to encourage cell regrowth. The composition can be designed to degrade as the cells develop into tissue. Temporary bulking can be achieved by using a fully or partially degradable composition or a composition that degrades in response to an applied condition, such as a change in temperature or pH.

The processes for using the compositions include dissolving the macromers in solution and delivering the solution to the intended site of bulking, using a delivery device such as a catheter or syringe. The macromers form a crosslinked hydrogel. In one embodiment, the macromers are exposed to the crosslinking initiator before they are administered to the intended site of bulking. In one embodiment, the macromers are formed into the crosslinked hydrogel prior to implantation.

DETAILED DESCRIPTION OF THE INVENTION

The invention relates to compositions for use in tissue bulking and coating. More specifically, the invention relates to compositions including crosslinkable macromonomers (also referred to herein as macromers) that form hydrogels useful in tissue bulking and coating. The invention also relates to methods for tissue bulking and coating.

The term "bulking" as used herein refers to partially or fully bulking a tissue or partially or fully filling a biological cavity. The cavity can be preexisting or formed for the purpose. Bulking can be performed, for example, for reconstruction, augmentation, or replacement of body tissue. Examples of bulking include bulking of the lower esophageal sphincter to treat GERD, urethral bulking to treat urinary incontinence, bulking of the ureteral bud to treat vesicoureteral reflux, esophageal bulking, tissue reconstruction due to injury or disease (i.e. reconstruction of a breast after partial mastectomy), tissue augmentation, and spinal disc replacement.

The term "sealing" as used herein refers to partially or fully covering a tissue or cell with the biomaterial. Sealing can be performed, for example, for adhesion prevention, to promote adhesion between surfaces, or for tissue or cellular encapsulation.

The compositions include macromers having a backbone of a polymer comprising units with a 1,2-diol and/or 1,3-diol structure and having at least two pendant chains including a crosslinkable group and optionally other pendant chains containing modifiers. The macromers form a hydrogel when crosslinked.

The compositions can be produced very simply and efficiently due to a number of factors. Firstly, the starting materials, such as the polymer backbones, are inexpensive to obtain or prepare. Secondly, the macromers are stable, so that they can be subjected to very substantial purification. The crosslinking can therefore be carried out using a macromer that is highly pure, containing substantially no unpolymerized constituents. Furthermore, the crosslinking can be carried out in purely aqueous solutions.

I. The Bulking and Coating Compositions

The Macromer Backbone

The macromers have a backbone of a polymer comprising units having a 1,2-diol or 1,3-diol structure, such as a polyhydroxy polymer. For example, polyvinyl alcohol (PVA) or copolymers of vinyl alcohol contain a 1,3-diol skeleton. The backbone can also contain hydroxyl groups in the form of 1,2-glycols, such as copolymer units of 1,2-dihydroxyethylene. These can be obtained, for example, by alkaline hydrolysis of vinyl acetate-vinylene carbonate copolymers. Other polymeric diols can be used, such as saccharides.

In addition, the macromers can also contain small proportions, for example, up to 20%, preferably up to 5%, of comonomer units of ethylene, propylene, acrylamide, methacrylamide, dimethacrylamide, hydroxyethyl methacrylate, alkyl methacrylates, alkyl methacrylates which are substituted by hydrophilic groups, such as hydroxyl, carboxyl or amino groups, methyl acrylate, ethyl acrylate, vinylpyrrolidone, hydroxyethyl acrylate, allyl alcohol, styrene, polyalkylene glycols, or similar comonomers usually used.

Polyvinyl alcohols that can be used as macromer backbones include commercially available PVAs, for example Vinol® 107 from Air Products (MW 22,000 to 31,000, 98 to 98.8% hydrolyzed), Polysciences 4397 (MW 25,000, 98.5% hydrolyzed), BF 14 from Chan Chun, Elvanol® 90-50 from DuPont and UF-120 from Unitika. Other producers are, for example, Nippon Gohsei (Gohsenol®), Monsanto (Gelvatol®), Wacker (Polyviol®), Kuraray, Deriki, and Shin-Etsu. In some cases it is advantageous to use Mowiol® products from Hoechst, in particular those of the 3-83, 4-88, 4-98, 6-88, 6-98, 8-88, 8-98, 10-98, 20-98, 26-88, and 40-88 types.

It is also possible to use copolymers of hydrolyzed or partially hydrolyzed vinyl acetate, which are obtainable, for example, as hydrolyzed ethylene-vinyl acetate (EVA), or vinyl chloride-vinyl acetate, N-vinylpyrrolidone-vinyl acetate, and maleic anhydride-vinyl acetate. If the macromer backbones are, for example, copolymers of vinyl acetate and vinylpyrrolidone, it is again possible to use commercially available copolymers, for example the commercial products available under the name Luviskol® from BASF. Particular examples are Luviskol VA 37 HM, Luviskol VA 37 E and Luviskol VA 28. If the macromer backbones are polyvinyl acetates, Mowilith 30 from Hoechst is particularly suitable.

Poly(vinyl alcohols) that can be derivatized as described herein preferably have a molecular weight of at least about 2,000. As an upper limit, the PVA may have a molecular weight of up to 1,000,000. Preferably, the PVA has a molecular weight of up to 300,000, especially up to approximately 130,000, and especially preferably up to approximately 60,000.

The PVA usually has a poly(2-hydroxy)ethylene structure. The PVA derivatized in accordance with the disclosure may, however, also comprise hydroxy groups in the form of 1,2-glycols.

The PVA system can be a fully hydrolyzed PVA, with all repeating groups being —$CH_2$—CH(OH), or a partially hydrolyzed PVA with varying proportions (1% to 25%) of pendant ester groups. PVA with pendant ester groups have repeating groups of the structure $CH_2$—CH(OR) where R is $COCH_3$ group or longer alkyls, as long as the water solubility of the PVA is preserved. The ester groups can also be substituted by acetaldehyde or butyraldehyde acetals that impart a certain degree of hydrophobicity and strength to the PVA. For an application that requires an oxidatively stable PVA, the commercially available PVA can be broken down by $NaIO_4$—$KMnO_4$ oxidation to yield a small molecular weight (2000 to 4000) PVA.

The PVA is prepared by basic or acidic, partial or virtually complete hydrolysis of polyvinyl acetate. In a preferred embodiment, the PVA comprises less than 50% of vinyl acetate units, especially less than about 25% of vinyl acetate units. Preferred amounts of residual acetate units in the PVA, based on the sum of vinyl alcohol units and acetate units, are approximately from 3 to 25%.

Crosslinkable Groups

The macromers have at least two pendant chains containing groups that can be crosslinked. The term group includes single polymerizable moieties, such as an acrylate, as well as larger crosslinkable regions, such as oligomeric or polymeric regions. The crosslinkers are desirably present in an amount of from approximately 0.01 to 10 milliequivalents of crosslinker per gram of backbone (meq/g), more desirably about 0.05 to 1.5 meq/g. The macromers can contain more than one type of crosslinkable group.

The pendant chains are attached via the hydroxyl groups of the backbone. Desirably, the pendant chains having crosslinkable groups are attached via cyclic acetal linkages to the 1,2-diol or 1,3-diol hydroxyl groups.

Crosslinking of the macromers may be via any of a number of means, such as physical crosslinking or chemical crosslinking. Physical crosslinking includes, but is not limited to, complexation, hydrogen bonding, desolvation, Van der wals interactions, and ionic bonding. Chemical crosslinking can be accomplished by a number of means including, but not limited to, chain reaction (addition) polymerization, step reaction (condensation) polymerization and other methods of increasing the molecular weight of polymers/oligomers to very high molecular weights. Chain reaction polymerization includes, but is not limited to, free radical polymerization (thermal, photo, redox, atom transfer polymerization, etc.), cationic polymerization (including onium), anionic polymerization (including group transfer polymerization), certain types of coordination polymerization, certain types of ring opening and metathesis polymerizations, etc. Step reaction polymerizations include all polymerizations which follow step growth kinetics including but not limited to reactions of nucleophiles with electrophiles, certain types of coordination polymerization, certain types of ring opening and metathesis polymerizations, etc. Other methods of increasing molecular weight of polymers/oligomers include but are not limited to polyelectrolyte formation, grafting, ionic crosslinking, etc.

Various crosslinkable groups are known to those skilled in the art and can be used, according to what type of crosslinking is desired. For example, hydrogels can be formed by the ionic interaction of divalent cationic metal ions (such as $Ca^{+2}$ and $Mg^{+2}$) with ionic polysaccharides such as alginates, xanthan gums, natural gum, agar, agarose, carrageenan, fucoidan, furcellaran, laminaran, hypnea, eucheuma, gum arabic, gum ghatti, gum karaya, gum tragacanth, locust beam gum, arabinogalactan, pectin, and amylopectin. Multifunctional cationic polymers, such as poly(l-lysine), poly(allylamine), poly(ethyleneimine), poly (guanidine), poly(vinyl amine), which contain a plurality of amine functionalities along the backbone, may be used to further induce ionic crosslinks.

Hydrophobic interactions are often able to induce physical entanglement, especially in polymers, that induces increases in viscosity, precipitation, or gelation of polymeric solutions. Block and graft copolymers of water soluble and insoluble polymers exhibit such effects, for example, poly (oxyethylene)-poly(oxypropylene) block copolymers, copolymers of poly(oxyethylene) with poly(styrene), poly (caprolactone), poly(butadiene), etc.

Solutions of other synthetic polymers such as poly(N-alkylacrylamides) also form hydrogels that exhibit thermoreversible behavior and exhibit weak physical crosslinks on warming. A two component aqueous solution system may be selected so that the first component (among other components) consists of poly(acrylic acid) or poly (methacrylic acid) at an elevated pH of around 8–9 and the other component consists of (among other components) a solution of poly(ethylene glycol) at an acidic pH, such that the two solutions on being combined in situ result in an immediate increase in viscosity due to physical crosslinking.

Other means for polymerization of the macromers also may be advantageously used with macromers that contain groups that demonstrate activity towards functional groups such as amines, imines, thiols, carboxyls, isocyanates, urethanes, amides, thiocyanates, hydroxyls, etc., which may be naturally present in, on, or around tissue. Alternatively, such functional groups optionally may be provided in some of the macromers of the composition. In this case, no external initiators of polymerization are needed and polymerization proceeds spontaneously when two complementary reactive functional groups containing moieties interact at the application site.

Desirable crosslinkable groups include (meth)acrylamide, (meth)acrylate, styryl, vinyl ester, vinyl ketone, vinyl ethers, etc. Particularly desirable are ethylenically unsaturated functional groups.

Ethylenically unsaturated groups can be crosslinked via free radical initiated polymerization, including via photoinitiation, redox initiation, and thermal initiation. Systems employing these means of initiation are well known to those skilled in the art. In one embodiment, a two part redox system is employed. One part of the system contains a reducing agent such as a ferrous salt. Various ferrous salts can be used, such as, for example, ferrous gluconate dihydrate, ferrous lactate dihydrate, or ferrous acetate. The other half of the solution contains an oxidizing agent such as hydrogen peroxide. Either or both of the redox solutions can contain macromer, or it may be in a third solution. The two solutions are combined to initiate the crosslinking.

Other reducing agents can be used, such as, but not limited to, cuprous salts, cerous salts, cobaltous salts, permanganate, and manganous salts. Ascorbate, for example, can be used as a coreductant to recycle the reductant and reduce the amount needed. This can reduce the toxicity of a ferrous based system. Other oxidizing agents that can be used include, but are not limited to, t-butyl hydroperoxide, t-butyl peroxide, benzoyl peroxide, cumyl peroxide, etc.

Specific Macromers

Specific macromers that are suitable for use in the compositions are disclosed in U.S. Pat. Nos. 5,508,317, 5,665,840, 5,807,927, 5,849,841, 5,932,674, 5,939,489, and 6,011,077.

In one embodiment, units containing a crosslinkable group conform, in particular, to the formula I

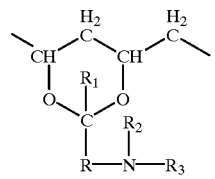

in which R is a linear or branched $C_1$–$C_8$ alkylene or a linear or branched $C_1$–$C_{12}$ alkane. Suitable alkylene examples include octylene, hexylene, pentylene, butylene, propylene, ethylene, methylene, 2-propylene, 2-butylene and 3-pentylene. Preferably lower alkylene R has up to 6 and especially preferably up to 4 carbon atoms. The groups ethylene and butylene are especially preferred. Alkanes include, in particular, methane, ethane, n- or isopropane, n-, sec- or tert-butane, n- or isopentane, hexane, heptane, or octane. Preferred groups contain one to four carbon atoms, in particular one carbon atom.

$R_1$ is hydrogen, a $C_1$–$C_6$ alkyl, or a cycloalkyl, for example, methyl, ethyl, propyl or butyl and $R_2$ is hydrogen or a $C_1$–$C_6$ alkyl, for example, methyl, ethyl, propyl or butyl. $R_1$ and $R_2$ are preferably each hydrogen.

$R_3$ is an olefinically unsaturated electron attracting copolymerizable radical having up to 25 carbon atoms. In one embodiment, $R_3$ has the structure

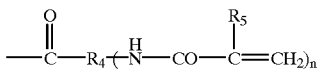

where $R_4$ is the

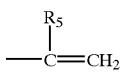

group if n=zero, or the

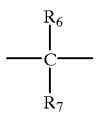

bridge if n=1;

$R_5$ is hydrogen or $C_1$–$C_4$ alkyl, for example, n-butyl, n- or isopropyl, ethyl, or methyl;

n is zero or 1, preferably zero; and $R^6$ and $R_7$, independently of one another, are hydrogen, a linear or branched $C_1$–$C_8$ alkyl, aryl or cyclohexyl, for example one of the following: octyl, hexyl, pentyl, butyl, propyl, ethyl, methyl, 2-propyl, 2-butyl or 3-pentyl. $R_6$ is preferably hydrogen or the $CH_3$ group, and $R_7$ is preferably a $C_1$–$C_4$ alkyl group. $R_6$ and $R_7$ as aryl are preferably phenyl.

In another embodiment, $R_3$ is an olefinically unsaturated acyl group of formula $R_8$—CO—, in which $R_8$ is an olefinically unsaturated copolymerizable group having from 2 to 24 carbon atoms, preferably from 2 to 8 carbon atoms, especially preferably from 2 to 4 carbon atoms. The olefinically unsaturated copolymerizable radical $R_8$ having from 2 to 24 carbon atoms is preferably alkenyl having from 2 to 24 carbon atoms, especially alkenyl having from 2 to 8 carbon atoms and especially preferably alkenyl having from 2 to 4 carbon atoms, for example ethenyl, 2-propenyl, 3-propenyl, 2-butenyl, hexenyl, octenyl or dodecenyl. The groups ethenyl and 2-propenyl are preferred, so that the group —CO—$R_8$ is the acyl radical of acrylic or methacrylic acid.

In another embodiment, the group $R_3$ is a radical of formula

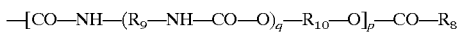

wherein p and q are zero or one and $R_9$ and $R_{10}$ are each independently lower alkylene having from 2 to 8 carbon atoms, arylene having from 6 to 12 carbon atoms, a saturated divalent cycloaliphatic group having from 6 to 10 carbon atoms, arylenealkylene or alkylenearylene having from 7 to 14 carbon atoms or arylenealkylenearylene having from 13 to 16 carbon atoms, and $R_8$ is as defined above.

Lower alkylene $R_9$ or $R_{10}$ preferably has from 2 to 6 carbon atoms and is especially straight-chained. Suitable examples include propylene, butylene, hexylene, dimethylethylene and, especially preferably, ethylene.

Arylene $R_9$ or $R_{10}$ is preferably phenylene that is unsubstituted or is substituted by lower alkyl or lower alkoxy, especially 1,3-phenylene or 1,4-phenylene or methyl-1,4-phenylene.

A saturated divalent cycloaliphatic group $R_9$ or $R_{10}$ is preferably cyclohexylene or cyclohexylene-lower alkylene, for example cyclohexylenemethylene, that is unsubstituted or is substituted by one or more methyl groups, such as, for example, trimethylcyclohexylenemethylene, for example the divalent isophorone radical.

The arylene unit of alkylenearylene or arylenealkylene $R_9$ or $R_{10}$ is preferably phenylene, unsubstituted or substituted by lower alkyl or lower alkoxy, and the alkylene unit thereof is preferably lower alkylene, such as methylene or ethylene, especially methylene. Such radicals $R_9$ or $R_{10}$ are therefore preferably phenylenemethylene or methylenephenylene.

Arylenealkylenearylene $R_9$ or $R_{10}$ is preferably phenylene-lower alkylene-phenylene having up to 4 carbon atoms in the alkylene unit, for example phenyleneethylenephenylene.

The groups $R_9$ and $R_{10}$ are each independently preferably lower alkylene having from 2 to 6 carbon atoms, phenylene, unsubstituted or substituted by lower alkyl, cyclohexylene or cyclohexylene-lower alkylene, unsubstituted or substituted by lower alkyl, phenylene-lower alkylene, lower alkylene-phenylene or phenylene-lower alkylenephenylene.

The group —$R_9$—NH—CO—O— is present when q is one and absent when q is zero. Macromers in which q is zero are preferred.

The group —CO—NH—($R_9$—NH—CO—O)$_q$—$R_{10}$—O— is present when p is one and absent when p is zero. Macromers in which p is zero are preferred.

In macromers in which p is one, q is preferably zero. Macromers in which p is one, q is zero, and $R_{10}$ is lower alkylene are especially preferred.

All of the above groups can be monosubstituted or polysubstituted, examples of suitable substituents being the following: $C_1$–$C_4$ alkyl, such as methyl, ethyl or propyl, —COOH, —OH, —SH, $C_1$–$C_4$ alkoxy (such as methoxy, ethoxy, propoxy, butoxy, or isobutoxy), —NO$_2$, —NH$_2$, —NH($C_1$–$C_4$), —NH—CO— NH$_2$, —N($C_1$–$C_4$ alkyl)$_2$, phenyl (unsubstituted or substituted by, for example, —OH or halogen, such as Cl, Br or especially I), —S($C_1$–$C_4$ alkyl), a 5- or 6-membered heterocyclic ring, such as, in particular, indole or imidazole, —NH—C(NH)—NH$_2$, phenoxyphenyl (unsubstituted or substituted by, for example, —OH or halogen, such as Cl, Br or especially I), an olefinic group, such as ethylene or vinyl, and CO—NH—C(NH)—NH$_2$.

Preferred substituents are lower alkyl, which here, as elsewhere in this description, is preferably $C_1$–$C_4$ allyl, $C_1$–$C_4$ alkoxy, COOH, SH, —NH$_2$, —NH($C_1$–$C_4$ alkyl), —N($C_1$–$C_4$ alkyl)$_2$ or halogen. Particular preference is given to $C_1$–$C_4$ alkyl, $C_1$–$C_4$ alkoxy, COOH and SH.

For the purposes of this invention, cycloalkyl is, in particular, cycloalkyl, and aryl is, in particular, phenyl, unsubstituted or substituted as described above.

Modifiers

The macromers can include further modifier groups and crosslinkable groups. Some such groups are described in U.S. Pat. Nos. 5,508,317, 5,665,840, 5,807,927, 5,849,841, 5,932,674, 5,939,489, and 6,011,077. Crosslinkable groups and the optional further modifier groups can be bonded to the macromer backbone in various ways, for example through a certain percentage of the 1,3-diol units being modified to give a 1,3-dioxane, which contains a crosslinkable group, or a further modifier, in the 2-position. Modifiers that might be attached to the backbone include those to modify the hydrophobicity, active agents or groups to allow attachment of active agents, photoinitiators, modifiers to enhance or reduce adhesiveness, modifiers to impart thermoresponsiveness, modifiers to impart other types of responsiveness, and additional crosslinking groups. These modifiers may be attached to the backbone, or to other monomeric units included in the backbone.

Attaching a cellular adhesion promoter to the macromers can enhance cellular attachment or adhesiveness of the bulking and coating agents formed by the compositions. These agents are well known to those skilled in the art and include carboxymethyl dextran, proteoglycans, collagen, gelatin, glucosaminoglycans, fibronectin, lectins, polycations, and natural or synthetic biological cell adhesion agents such as RGD peptides.

Having pendant ester groups that are substituted by acetaldehyde or butyraldehyde acetals, for example, can increase the hydrophobicity of the macromers and the formed hydrogel. Hydrophobic groups can desirably be present in an amount from about 0 to 25%.

It may also be desirable to include on the macromer a molecule that allows visualization of the formed hydrogel. Examples include dyes and molecules visualizable by magnetic resonance imaging.

Degradable Regions

The macromers can form a hydrogel that is degradable. Suitable degradable systems are described in U.S. patent application Ser. No. 09/714,700, titled "Degradable Poly (Vinyl Alcohol) Hydrogels" and filed on Nov. 15, 2000. In the degradable systems described in that application, the macromers include a degradable region in the backbone or on a pendant chain. The degradable region is preferably degradable under in vivo conditions by hydrolysis. The degradable region can be enzymatically degradable. For example, the degradable region may be polymers and oligomers of glycolide, lactide, $\epsilon$-caprolactone, other hydroxy acids, and other biologically degradable polymers that yield materials that are non-toxic or present as normal metabolites in the body. Preferred poly($\alpha$-hydroxy acids) are poly (glycolic acid), poly(DL-lactic acid) and poly(L-lactic acid). Other useful materials include poly(amino acids), poly (anhydrides), poly(orthoesters), poly(phosphazines), and poly(phosphoesters). Polylactones such as poly($\epsilon$-caprolactone), poly($\epsilon$-caprolactone), poly($\delta$-valerolactone) and poly($\gamma$-butyrolactone), for example, are also useful. Enzymatically degradable linkages include poly(amino acids), gelatin, chitosan, and carbohydrates. The biodegradable regions may have a degree of polymerization ranging from one up to values that would yield a product that was not substantially water soluble. Thus, monomeric, dimeric, trimeric, oligomeric, and polymeric regions may be used. The biodegradable region could, for example, be a single methacrylate group.

Biodegradable regions can be constructed from polymers or monomers using linkages susceptible to biodegradation, such as ester, acetal, carbonate, peptide, anhydride, orthoester, phosphazine, and phosphoester bonds. The biodegradable regions may be arranged within the macromers such that the formed hydrogel has a range of degradability, both in terms of extent of degradation, whether complete or partial, and in terms of time to complete or partial degradation.

Synthesis of Macromers

The macromers can be made by general synthetic methods known to those skilled in the art. The specific macromers discussed above can be made as described in U.S. Pat. Nos. 5,508,317, 5,665,840, 5,807,927, 5,849,841, 5,932,674, 5,939,489, and 6,011,077.

The specific macromers described above are extraordinarily stable. Spontaneous crosslinking by homopolymerization does not typically occur. The macromers can furthermore be purified in a manner known per se, for example by precipitation with organic solvents, such as acetone, extraction in a suitable solvent, washing, dialysis, filtration, or ultrafiltration. Ultrafiltration is especially preferred. By means of the purification process the macromers can be obtained in extremely pure form, for example in the form of concentrated aqueous solutions that are free, or at least substantially free, from reaction products, such as salts, and from starting materials.

The preferred purification process for the macromers of the invention, ultrafiltration, can be carried out in a manner known per se. It is possible for the ultrafiltration to be carried out repeatedly, for example from two to ten times. Alternatively, the ultrafiltration can be carried out continuously until the selected degree of purity is attained. The selected degree of purity can in principle be as high as desired. A suitable measure for the degree of purity is, for example, the sodium chloride content of the solution, which can be determined simply in a known manner, such as by conductivity measurements.

The macromers are crosslinkable in an extremely effective and controlled manner.

Vinylic Comonomers

The process for polymerization of the macromers may comprise, for example, crosslinking a macromer comprising units of formula I, especially in substantially pure form, that is to say, for example, after single or repeated ultrafiltration, preferably in solution, especially in aqueous solution, in the absence or presence of an additional vinylic comonomer.

The vinylic comonomer may be hydrophilic or hydrophobic, or a mixture of a hydrophobic and a hydrophilic vinylic monomer. Generally, approximately from 0.01 to 80 units of a typical vinylic comonomer react per unit of formula I, especially from 1 to 30 units per unit of formula I, and especially preferably from 5 to 20 units per unit of formula I.

It is also preferable to use a hydrophobic vinylic comonomer or a mixture of a hydrophobic vinylic comonomer with a hydrophilic vinylic comonomer, the mixture comprising at least 50 percent by weight of a hydrophobic vinylic comonomer. In that manner the mechanical properties of the polymer can be improved without the water content falling substantially. In principle, however, both conventional hydrophobic vinylic comonomers and conventional hydrophilic vinylic comonomers are suitable for copolymerization with the macromer.

Suitable hydrophobic vinylic comonomers include, without the list being exhaustive, $C_1$–$C_{18}$ alkyl acrylates and methacrylates, $C_3$–$C_{18}$ alkyl acrylamides and methacrylamides, acrylonitrile, methacrylonitrile, vinyl-$C_1$–$C_{18}$ alkanoates, $C_2$–$C_{18}$ alkenes, $C_2$–$C_{18}$ haloalkenes, styrene, $C_1$–$C_6$ alkylstyrene, vinyl alkyl ethers, in which the alkyl moiety contains from 1 to 6 carbon atoms, $C_2$–$C_{10}$ perfluoroalkyl acrylates and methacrylates or correspondingly partially fluorinated acrylates and methacrylates, $C_3$–$C_{12}$ perfluoroalkyl-ethylthiocarbonylaminoethyl acrylates and methacrylates, acryloxy- and methacryloxy-alkylsiloxanes, N-vinylcarbazole, $C_3$–$C_{12}$ alkyl esters of maleic acid, fumaric acid, itaconic acid, mesaconic acid and the like. $C_1$–$C_4$ alkyl esters of vinylically unsaturated carboxylic acids having from 3 to 5 carbon atoms or vinyl esters of carboxylic acids having up to 5 carbon atoms, for example, are preferred.

Examples of suitable hydrophobic vinylic comonomers include methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl methacrylate, tris-trimethylsilyloxy-silyl-propyl methacrylate, 3-methacryloxypropylpentamethyldisiloxane and bis(methacryloxypropyl)tetramethyldisiloxane.

Suitable hydrophilic vinylic comonomers include, without the list being exhaustive, hydroxy-substituted lower alkyl acrylates and methacrylates, acrylamide, methacrylamide, lower alkyl acrylamides and methacrylamides, ethoxylated acrylates and methacrylates, hydroxy-substituted lower alkyl acrylamides and methacrylamides, hydroxy-substituted lower alkyl vinyl ethers, sodium ethylenesulfonate, sodium styrenesulfonate, 2-acrylamido-2-methylpropanesulfonic acid (AMPS® monomer from Lubrizol Corporation), N-vinylpyrrole, N-vinylsuccinimide, N-vinylpyrrolidone, 2- or 4-vinylpyridine, acrylic acid, methacrylic acid, amino- (the term "amino" also including quaternary ammonium), mono-lower alkylamino- or di-lower alkylamino-lower alkyl acrylates and methacrylates, allyl alcohol and the like. Hydroxy-substituted $C_2$–$C_4$ alkyl(meth)acrylates, five- to seven-membered N-vinyl lactams, N,N-di-$C_1$–$C_4$ alkyl(meth)acrylamides and vinylically unsaturated carboxylic acids having a total of from 3 to 5 carbon atoms, for example, are preferred.

Contrast Agents

It may be desirable to include a contrast agent in the compositions. A contrast agent is a biocompatible (non-toxic) material capable of being monitored by, for example, radiography. The contrast agent can be water soluble or water insoluble. Examples of water soluble contrast agents include metrizamide, iopamidol, iothalamate sodium, iodomide sodium, and meglumine. Iodinated liquid contrast agents include Omnipaque®, Visipaque®, and Hypaque-76®. Examples of water insoluble contrast agents are tantalum, tantalum oxide, barium sulfate, gold, tungsten, and platinum. These are commonly available as particles preferably having a size of about 10 μm or less.

The contrast agent can be added to the compositions prior to administration. Both solid and liquid contrast agents can be simply mixed with a solution of the liquid compositions or with the solid articles. Liquid contrast agent can be mixed at a concentration of about 10 to 80 volume percent, more desirably about 20 to 50 volume percent. Solid contrast agents are desirably added in an amount of about 10 to 40 weight percent, more preferably about 20 to 40 weight percent.

Active Agents

An effective amount of one or more biologically active agents can be included in the compositions. It may be desirable to deliver the active agent from the formed hydrogel. Biologically active agents that it may be desirable to deliver include prophylactic, therapeutic, and diagnostic agents including organic and inorganic molecules and cells (collectively referred to herein as an "active agent" or "drug"). A wide variety of active agents can be incorporated into the hydrogel. Release of the incorporated additive from the hydrogel is achieved by diffusion of the agent from the hydrogel, degradation of the hydrogel, and/or degradation of a chemical link coupling the agent to the polymer. In this context, an "effective amount" refers to the amount of active agent required to obtain the desired effect.

Examples of active agents that can be incorporated include, but are not limited to, anti-angiogenic agents, growth factors, chemotherapeutic agents, radiation delivery devices, such as radioactive seeds for brachytherapy, and gene therapy compositions.

Chemotherapeutic agents that can be incorporated include water soluble chemotherapeutic agents, such as cisplatin (platinol), doxorubicin (adriamycin, rubex), or mitomycin C (mutamycin). Other chemotherapeutic agents include iodinated fatty acid ethyl esters of poppy seed oil, such as lipiodol.

Cells can be incorporated into the compositions, including cells to encourage tissue growth or cells to secrete a desired active agent. For example, cells that can be incorporated include fibroblasts, endothelial cells, muscle cells, stem cells, etc. Cells can be modified to secrete active agents such as growth factors.

Active agents can be incorporated into the liquid compositions simply by mixing the agent with the composition prior to administration. The active agent will then be entrapped in the hydrogel that is formed upon administration of the composition. Active agents can be incorporated into the preformed articles through encapsulation and other methods known in the art and discussed further below. The active agent can be in compound form or can be in the form of degradable or nondegradable nano or microspheres. It some cases, it may be possible and desirable to attach the active agent to the macromer or to the preformed article. The active agent may also be coated onto the surface of the preformed article. The active agent may be released from the macromer or hydrogel over time or in response to an environmental condition.

Other Additives

It may be desirable to include a peroxide stabilizer in redox initiated systems. Examples of peroxide stabilizers are Dequest® products from Solutia Inc., such as for example Dequest® 2010 and Dequest® 2060S. These are phosphonates and chelants that offer stabilization of peroxide systems. Dequest® 2060S is diethylenetriamine penta (methylene phosphonic acid). These can be added in amounts as recommended by the manufacturer.

It may be desirable to include fillers in the compositions, such as fillers that leach out of the formed hydrogel over a period of time and cause the hydrogel to become porous. Such may be desirable, for example, where the composition is used for chemotherapy and it may be desirable to administer a follow up dose of chemoactive agent. Appropriate fillers include calcium salts, for example.

Characteristics That Can Be Modified

The compositions are highly versatile. A number of characteristics can be easily modified, making the compositions suitable for a number of applications. For example, as discussed above, the polymer backbones can include comonomers to add desired properties, such as, for example, thermoresponsiveness, degradability, gelation speed, and hydrophobicity. Modifiers can be attached to the polymer backbone (or to pendant groups) to add desired properties, such as, for example, thermoresponsiveness, degradability, hydrophobicity, and adhesiveness. Active agents can also be attached to the polymer backbone using the free hydroxyl groups, or can be attached to pendant groups.

The gelation time of the liquid compositions can be varied from about 0.5 seconds to as long as 10 minutes, and longer if desired. A longer gelation time will generally be required if crosslinking is initiated a distance from the intended application site.

The gelation time will generally be affected by, and can be modified by changing at least the following variables: the initiator system, crosslinker density, macromer molecular weight, macromer concentration (solids content), and type of crosslinker. A higher crosslinker density will provide faster gelation time; a lower molecular weight will provide a slower gelation time. A higher solids content will provide faster gelation time. For redox systems the gelation time can be designed by varying the concentrations of the redox components. Higher reductant and higher oxidant will provide faster gelation, higher buffer concentration and lower pH will provide faster gelation.

The firmness of the formed hydrogel will be determined in part by the hydrophilic/hydrophobic balance, where a higher hydrophobic percent provides a firmer hydrogel. The firmness will also be determined by the crosslinker density (higher density provides a firmer hydrogel), the macromer molecular weight (lower MW provides a firmer hydrogel), and the length of the crosslinker (a shorter crosslinker provides a firmer hydrogel).

The swelling of the hydrogel is inversely proportional to the crosslinker density. Generally, no or minimal swelling is desired, desirably less than about 10 percent.

Elasticity of the formed hydrogel can be increased by increasing the size of the backbone between crosslinks and decreasing the crosslinker density. Incomplete crosslinking will also provide a more elastic hydrogel. Preferably the elasticity of the hydrogel substantially matches the elasticity of the tissue to which the composition is to administered.

Making Preformed Bulking and Sealing Articles

Preformed articles are made, in general, by dissolving macromers in an appropriate solvent, shaping the macromers such as by pouring the macromer solution in a mold, if desired, and crosslinking the macromers. A mold is suitable for use in making rod shaped articles, for example, or discs for use in spinal disc replacement.

Microparticles can be made by forming a hydrogel sheet and milling it into particles. Such particles will be irregular in size and shape.

In one embodiment, the preformed articles are spherical microparticles termed microspheres. Microspheres can be made by a number of techniques known to those skilled in the art, such as single and double emulsion, suspension polymerization, solvent evaporation, spray drying, and solvent extraction. Methods for making microspheres are described in the literature, for example, in Mathiowitz and Langer, J. Controlled Release 5:13–22 (1987); Mathiowitz et al., Reactive Polymers 6:275–283 (1987); Mathiowitz et al., J. Appl. Polymer Sci. 35:755–774 (1988); Mathiowitz et al., Scanning Microscopy 4:329–340 (1990); Mathiowitz et al., J. Appl. Polymer Sci., 45:125–134 (1992); and Benita et al., J. Pharm. Sci. 73:1721–1724 (1984).

In solvent evaporation, described for example in Mathiowitz et al., (1990), Benita et al. (1984), and U.S. Pat. No. 4,272,398, the macromers are dissolved in a solvent. If desired, an agent to be incorporated, either in soluble form or dispersed as fine particles, is added to the macromer solution, and the mixture is suspended in an aqueous phase that contains a surface active agent. The resulting emulsion is stirred until most of the solvent evaporates, leaving solid microspheres, which may be washed with water and dried overnight in a lyophilizer. The microspheres are polymerized, for example, by exposure to light.

In solvent removal, the macromers are dissolved in a solvent. The mixture can then be suspended in oil, such as silicon oil, by stirring, to form an emulsion. As the solvent diffuses into the oil phase, the emulsion droplets harden into solid polymer microspheres. The microspheres can be polymerized by exposure to light, for example.

Spray drying is implemented by passing the polymerizable macromers used to form the hydrogel through a nozzle, spinning disk or equivalent device to atomize the mixture to form fine droplets. The polymerizable macromers may be provided in a solution or suspension, such as an aqueous solution. The fine droplets are exposed to light, for example, to cause polymerization of the macromer and formation of the hydrogel microspheres.

In another embodiment, hydrogel particles are prepared by a water-in-oil emulsion or suspension process, wherein the polymerizable macromers and the substance to be incorporated, if desired, are suspended in a water-in-oil suspension and exposed to light to polymerize the macromers to form hydrogel particles incorporating the substance, such as a biologically active agent.

In another embodiment, microspheres can be formed by atomizing macromer solution into oil, followed by polymerization.

There are many variables that affect the size, size distribution, and quality of the microspheres formed. An important variable is the choice of stabilizer. Good stabilizers have an HLB number from 1 to 4 and have some solubility in the oil phase. Some appropriate stabilizers include cellulose acetate butyrate (with 17% butyrate), sorbitan oleates, and dioctylsulphosuccinate. The amount and type of stabilizer will control the particle size and reduce coalescing of the particles during crosslinking. The oil can be a water-insoluble oil such as liquid paraffin, but water-insoluble halogenated solvents such as dichloroethane are commonly used. The ratio of water to oil is also important and desirably ranges from about 1:1 to 1:4.

Microspheres can be made in sizes ranging from about 10 microns to 2000 microns. The process used to make the microspheres can be controlled to achieve a particular desired size range of microspheres. Other methods, such as sieving, can be used to even more tightly control the size range of the microspheres.

Active agents can be included in the microspheres as described above. It may be desirable to coat the microspheres in modifiers or active agents, such as, for example, agents to increase cellular attachment. Such coating can be done by methods known to those skilled in the art.

II. Methods of Using the Tissue Bulking and Coating Compositions

The compositions can be used for a variety of applications such as, but not limited to, bulking of the lower esophageal sphincter to treat GERD, urethral bulking to treat urinary incontinence, bulking of the ureteral bud to treat vesicoureteral reflux, esophageal bulking, tissue reconstruction due to injury or disease (i.e. reconstruction of a breast after partial mastectomy), tissue augmentation, spinal disc replacement, for adhesion prevention, to promote adhesion between surfaces, or for tissue or cellular encapsulation.

According to the general method, an effective amount of the composition is administered to the desired administration site. In one embodiment, the macromers are crosslinked in situ. In another embodiment, the macromers are formed into a hydrogel prior to administration. The term "effective amount", as used herein, means the quantity of composition needed to bulk or coat the biological structure of interest. The effective amount of composition administered to a particular patient will vary depending upon a number of factors, including the sex, weight, age, and general health of the patient, the type, concentration, and consistency of the macromers and the hydrogel that results from crosslinking, and the particular site and condition being treated. The macromers may be administered over a number of treatment sessions.

The methods of using the liquid compositions involve combining the components, including any comonomers and other additives, under conditions suitable for crosslinking of the macromers. The crosslinking is suitably carried out in a solvent. A suitable solvent is in principle any solvent that dissolves the macromers, for example water, alcohols, such as lower alkanols, for example ethanol or methanol, also carboxylic acid amides, such as dimethylformamide, or dimethyl sulfoxide, and also a mixture of suitable solvents, such as, for example, a mixture of water with an alcohol, such as, for example, a water/ethanol or a water/methanol mixture. The combination of the macromers is preferably carried out in a substantially aqueous solution. In accordance with the invention, the criterion that the macromer is soluble in water denotes in particular that the macromer is soluble in a concentration of approximately from 3 to 90 percent by weight, preferably approximately from 5 to 60 percent by weight, in a substantially aqueous solution. Insofar as it is possible in an individual case, macromer concentrations of more than 90 percent are also included in accordance with the invention.

Within the scope of this invention, substantially aqueous solutions of the macromer comprise especially solutions of the macromer in water, in aqueous salt solutions, especially in aqueous solutions that have an osmolarity of approximately from 200 to 450 milliosmol per 1000 ml (mOsm/l), preferably an osmolarity of approximately from 250 to 350 mOsm/l, especially approximately 300 mOsm/l, or in mixtures of water or aqueous salt solutions with physiologically tolerable polar organic solvents, such as, for example, glycerol. Solutions of the macromer in water or in aqueous salt solutions are preferred.

The viscosity of the solution of the macromer in the substantially aqueous solution is, within wide limits, not critical, but the solution should preferably be a flowable solution that can be delivered through an appropriately sized catheter, syringe, or spray device. For delivery through a microcatheter, a viscosity in the range of about 10 to 50 cp is desirable. The viscosity can be substantially higher for delivery through a syringe. The viscosity will generally be controlled by the molecular weight of the macromers, the solids content of the solution, and the type and amount of contrast agent present.

The solids content of the solution will preferably range from about 2 percent by weight to about 30 percent by weight, desirably from about 6 to 12 percent by weight.

In one embodiment, the macromers are crosslinkable via free radical polymerization. In one embodiment, the crosslinking initiator is mixed with the macromer solution before administration, during administration, or after administration. For example, a redox system can be mixed with the macromer solution at the time of administration. In one embodiment, the crosslinking initiator may be present at the site of administration. For example, the initiator could be a substance, such as charged blood components, present at the site. Macromers can be used that crosslink when they contact each other. These can be mixed before, during, or after administration. In one embodiment, the crosslinking initiator is an applied stimulus, such as light or heat, which causes crosslinking. Suitable initiators are known for thermal, photo, and redox initiated polymerization. In a redox initiated system employing ferrous ion, peroxide, and ascorbate, the desired amounts of the components will be determined by concerns related to gelation speed, toxicity, extent of gelation desired, and stability.

It may be desirable, if initiator is added before administration, to use a system that provides delayed crosslinking so that the composition does not gel too early. Moreover, using delayed curing, the composition can assume or be formed into a desired shape before complete curing has occurred.

In some embodiments, the composition should be injected before substantial crosslinking of the macromers has occurred. This allows the macromers to continue crosslinking in situ and prevents blockage of the syringe needle or catheter with gelled polymer. In addition, such in situ crosslinking may allow anchoring of the hydrogel to host tissue by covalently bonding with collagen molecules present within the host tissue.

Since the compositions preferably comprise no undesired low molecular weight constituents, the crosslinked hydrogel products also comprise no such constituents. The bulking and coating agents obtainable by the compositions are therefore distinguished, in an advantageous embodiment, by the fact that they are extremely clean.

The preformed bulking articles can be administered similarly to how solid bulking agents are presently administered. The microspheres will desirably be supplied in physiological, sterile saline. A microcatheter, for example, can be used to deliver the microspheres to the desired administration site. It may be desirable to mix a contrast agent and/or chemotherapeutic agent with the microspheres before administration.

Delivery Devices

The compositions can be delivered to the intended site of bulking or coating using methods known to those skilled in the art. Generally, a catheter, syringe, or spray device is used. In many cases, a multi-lumen catheter is used to deliver the composition to the intended site of administration. Generally, a two or three lumen catheter will be used, wherein the components of the composition which crosslink or initiate crosslinking are maintained in separate lumens until the time of administration. For example, in the case of a macromer that crosslinks via redox initiated free radical polymerization, one solution containing the reducing agent is delivered through a first lumen while a solution containing the oxidizing agent is delivered through a second lumen. The macromer can be in one or both of the solutions. A third lumen can be used to deliver contrast agent. A guidewire can be inserted through any of the lumens, and removed prior to delivery of a solution through that lumen.

In one embodiment, the catheter includes a mixing chamber at its end. A side by side "double D" lumen can be used, wherein the interior wall has been removed at the distal end to form an area where the two solutions combine before they are injected into the lumen or void. Alternatively, a coaxial catheter can be used, where one of the inner or outer lumens extends further than the other. Other types of multi-lumen catheters are disclosed in the art.

In one embodiment, a redox initiated macromer composition is used. Using a triple lumen catheter, a solution containing the reductant is introduced through one lumen, a solution containing the oxidant is introduced using a second lumen, and the third lumen is used for introducing liquid contrast to monitor the site before and after administration of the composition. The macromer can be in one of both of the reductant and oxidant solutions. Desirably, a contrast agent is present in one or both of the reductant or oxidant solutions so that administration of the composition can be monitored.

Tissue Regrowth

Examples of cells which can be implanted as described herein include chondrocytes and other cells that form cartilage, osteoblasts and other cells that form bone, muscle cells, fibroblasts, and organ cells. As used herein, "organ cells" includes hepatocytes, islet cells, cells of intestinal origin, cells derived from the kidney, and other cells acting primarily to synthesize and secret, or to metabolize materials.

Cells can be obtained directly from a donor, from cell culture of cells from a donor, or from established cell culture lines. Preferably, cells of the same species and preferably immunological profile are obtained by biopsy, either from the patient or a close relative, which are then grown to confluence in culture using standard conditions and used as needed. If cells that are likely to elicit an immune reaction are used, such as human muscle cells from immunologically distinct individual, then the recipient can be immunosuppressed as needed, for example, using a schedule of steroids and other immunosuppressant drugs such as cyclosporine. However, in the most preferred embodiment, the cells are autologous.

Cell attachment and viability can be assessed using scanning electron microscopy, histology, and quantitative assessment with radioisotopes. The function of the implanted cells can be determined using a combination of the above-techniques and functional assays as appropriate for the cell type.

This technique can be used to provide multiple cell types, including genetically altered cells. It can also be used for immunoprotection of cell transplants while a new tissue or tissue equivalent is growing by excluding the host immune system.

Preferably the isolated cells are suspended in the macromer solution to a concentration of between 1 and 50 million cells/ml, most preferably between 10 and 20 million cells/ml. The macromer/cell solution is then injected directly into the site where it is desired to implant the cells, prior to crosslinking of the macromers to form the hydrogel matrix. However, the matrix may also be molded and implanted in one or more different areas of the body to suit a particular application. This application is particularly relevant where a specific structural design is desired or where the area into which the cells are to be implanted lacks specific structure or support to facilitate growth and proliferation of the cells.

The site, or sites, where cells are to be implanted is determined based on individual need, as is the requisite number of cells. For cells having organ function, for example, hepatocytes or islet cells, the mixture can be injected into the mesentery, subcutaneous tissue, retroperitoneum, properitoneal space, and intramuscular space. For formation of cartilage, the cells are injected into the site where cartilage formation is desired. One could also apply an external mold to shape the injected solution. Additionally, by controlling the rate of polymerization, it is possible to mold the cell-hydrogel injected implant like one would mold clay. Alternatively, the mixture can be injected into a mold, the hydrogel allowed to harden, then the material implanted.

The suspension can be injected via a syringe and needle directly into a specific area wherever a bulking agent is desired, i.e., a soft tissue deformity such as that seen with areas of muscle atrophy due to congenital or acquired diseases or secondary to trauma, burns, and the like. An example of this would be the injection of the suspension in the upper torso of a patient with muscular atrophy secondary to nerve damage.

The suspension can also be injected as a bulking agent for hard tissue defects, such as bone or cartilage defects, either congenital or acquired disease states, or secondary to trauma, burns, or the like. An example of this would be an injection into the area surrounding the skull where a bony deformity exists secondary to trauma. The injunction in these instances can be made directly into the needed area with the use of a needle and syringe under local or general anesthesia.

The suspension could also be injected percutaneously by direct palpation, such as by placing a needle inside the vas deferens and occluding the same with the injected bulking substance, thus rendering the patient infertile. The suspension could also be injected through a catheter or needle with fluoroscopic, sonographic, computed tomography, magnetic resonance imaging or other type of radiologic guidance. This would allow for placement or injection of this substance either by vascular access or percutaneous access to specific organs or other tissue regions in the body, wherever a bulking agent would be required.

Further, this substance could be injected through a laparoscope or thoracoscope to any intraperitoneal or extraperitoneal or thoracic organ. For example, the suspension could be injected in the region of the gastroesophageal junction for the correcting of gastroesophageal reflux. This could be performed either with a thoracoscope injecting the substance in the esophageal portion of the gastroesophageal region, or via a laparoscope by injecting the substance in the gastric portion of the gastroesophageal region, or by a combined approach.

If the intent is to form new tissue, the macromer desirably is degradable and degrades at a rate sufficient to provide support to the cells while they form the desired tissue.

Tissue Coating

The compositions can be used for coating tissues using methods taught in U.S. Pat. No. 5,410,016 and WO 00/09087, for example. A spray delivery system can be used, wherein crosslinking of the macromers is initiated via photopolymerization or redox initiation. For example, a two part redox system can be used, wherein the device delivers a reductant component and an oxidant component, which cause crosslinking of the macromer when they mix. The device can deliver the components as overlapping sprays to ensure mixing. Alternatively, a device having a mixing chamber can be used.

EXAMPLES

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. In the examples, unless expressly stated otherwise, amounts and percentages are by weight, temperature is in degrees Celsius or is at ambient temperature, and pressure is at or near atmospheric. The examples are not intended to restrict the scope of the invention.

Example 1

Subcutaneous Injection Using Pig Bladder

Table 1 describes the formulations employed. The macromers were PVA of the molecular weights noted substituted with the noted amounts of N-acrylamidoacetaldehyde dimethyl acetal. The macromers were made substantially as described in U.S. Pat. No. 5,932,674. The formulations were as follows for 10 grams of 10% macromer solutions. The stock solutions were 41.5 $\mu$M Fe lactate; 415 $\mu$M peroxide, 1 M acetate buffer, pH 4.1, 415 $\mu$M ascorbate.

1) R (reductant): 300 $\mu$l Fe, 160 $\mu$l ascorbic acid, 200 $\mu$l acetate buffer O (oxidant): 160 $\mu$l peroxide, 200 $\mu$l buffer
2) R (reductant): 150 $\mu$l Fe, 160 $\mu$l ascorbic acid, 200 $\mu$l acetate buffer O (oxidant): 160 $\mu$l peroxide, 200 $\mu$l buffer
3) R (reductant): 600 $\mu$l Fe, 160 $\mu$l ascorbic acid, 400 $\mu$l acetate buffer O (oxidant): 400 $\mu$l peroxide, 400 $\mu$l buffer
4) R (reductant): 400 $\mu$l Fe, 160 $\mu$l ascorbic acid, 200 $\mu$l acetate buffer O (oxidant): 160 $\mu$l peroxide, 200 $\mu$l buffer

| sample | PVA | crosslinks per chain | formulation | gel time (sec) | firmness |
|---|---|---|---|---|---|
| 1 | 4-88 31 kDa | 6 | 2 | 7.70 | 1 (most firm) |
| 2 | 4-88 31 kDa | 6 | 3 | 2.94 | 1 |
| 3 | 3-83 14 kDa | 2.5 | 1 | 6.23 | 2 |
| 4 | 3-83 14 kDa | 2.5 | 4 | 5.38 | 2 |
| 5 | 3-83 14 kDa | 2 | 1 | 8.40 | 3 |
| 6 | 4-88 31 kDa | 3 | 1 | 8.47 | 4 |
| 7 | 4-88 31 kDa | 3 | 4 | 6.75 | 4 |
| 8 | 3-98 16 kDa | 2 | 1 | 16 | 5 (least firm) |

The compositions were injected into the subcutaneous space of freshly excised pig bladders. The device for injection included separate syringes for the reductant and oxidant solutions placed into a syringe manifold. One or more mixers were placed between female and male diffusers. A 20 gauge by 3.5 inch needle was used for final delivery. The compositions injected easily into the subcutaneous space to show demonstrable bulking with limited tracking as the needle was withdrawn. Sample 8 could be injected through a 22 gauge needle and through a 3 Fr single lumen catheter after crosslinking.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A tissue bulking composition comprising microspheres formed from macromers, wherein the macromers prior to crosslinking have a polymeric backbone comprising units with a 1,2-diol or 1,3-diol structure and at least two pendant chains bearing crosslinkable groups which are olefinically unsaturated groups, wherein the macromers are crosslinked via free radical polymerization to form a hydrogel.

2. The composition of claim 1, wherein the backbone polymer comprises a polyhydroxy polymer.

3. The composition of claim 1, wherein the pendant chains bearing crosslinkable groups are attached to the backbone via the 1,2-diol or 1,3-diol groups.

4. The composition of claim 3, wherein the pendant chains bearing crosslinkable groups are attached to the backbone via cyclic acetal linkages.

5. The composition of claim 1, wherein the polymer comprises poly(vinyl alcohol) (PVA) and copolymers thereof.

6. The composition of claim 1, wherein the macromers comprise units having the formula;

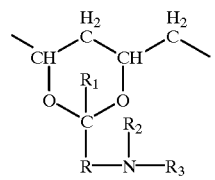

in which R is a linear or branched $C_1$–$C_8$ alkylene or a linear or branched $C_1$–$C_{12}$ alkane; $R_1$ is hydrogen, a $C_1$–$C_6$ alkyl, or a cycloalkyl; $R_2$ is hydrogen or a $C_1$–$C_6$ alkyl; and $R_3$ is an olefinically unsaturated electron attracting copolymerizable radical having up to 25 carbon atoms.

7. The composition of claim 1, wherein the macromers further comprise pendant modifier groups.

8. The composition of claim 1, further comprising an active agent.

9. The composition of claim 1, wherein the hydrogel is biodegradable.

10. The composition of claim 1, further comprising a contrast agent.

11. A method for tissue bulking comprising administering the microspheres of claim 1.

12. A method for tissue bulking comprising administering the microspheres of claim 6.

13. Hydrogel microspheres formed by free-radical polymerization of macromers, wherein the macromers have a polymeric backbone comprising units with a 1,2-diol or 1,3-diol structure and at least two pendant chains bearing crosslinkable groups which are olefinically unsaturated groups.

* * * * *